(12) United States Patent
Deber et al.

(10) Patent No.: US 8,546,527 B2
(45) Date of Patent: Oct. 1, 2013

(54) MOLECULAR WEIGHT MARKERS FOR MEMBRANE PROTEINS

(76) Inventors: Charles Deber, Toronto (CA); Arianna Rath, Toronto (CA); Vincent G. Nadeau, Toronto (CA)

(*) Notice: Subject to any disclaimer, the term of this patent is extended or adjusted under 35 U.S.C. 154(b) by 335 days.

(21) Appl. No.: 12/870,450

(22) Filed: Aug. 27, 2010

(65) Prior Publication Data
US 2011/0054147 A1    Mar. 3, 2011

Related U.S. Application Data

(60) Provisional application No. 61/237,840, filed on Aug. 28, 2009.

(51) Int. Cl.
*C07K 14/00*    (2006.01)
*C07K 9/00*    (2006.01)

(52) U.S. Cl.
USPC .......................... 530/326; 530/333; 530/300

(58) Field of Classification Search
None
See application file for complete search history.

(56) References Cited

PUBLICATIONS

Rath, et al. Novel hydrophobic standards for membrane protein molecular weight determinations on sodium dodecylsulfate polyacrylamide gel electrophoresis. Biochemistry, 2010. 49(50): p. 10589-10591.
Sato, et al. A simple method for preparation of molecular weight marker proteins for sodium dodecyl sulfate-polyacrylamide gel electrophoresis by photopolymerizations of hemoglobin subunits. Electrophoresis, 1988. 9(7): p. 352-3.
Choma, et al. Asparagine-mediated self-association of a model transmembrane helix. Nat Struct Biol, 2000. 7(2): p. 161-6.
Walkenhorst, et al. Polar residues in transmembrane helices can decrease electrophoretic mobility in polyacrylamide gels without causing helix dimeriazation. Biochim Biophys Acta, 1788(6): p. 1321-31.
Reynolds, et al. Binding of dodecyl sulfate to proteins at high binding ratios. Possible implications for the state of proteins in biological membranes. Proc Natl Acad Sci U S A, 1970. 66(3): p. 1002-7.
Shirahama et al. Free-boundary electrophoresis of sodium dodecyl sulfate-protein polypeptide complexes with special reference to SDS-polyacrylamide gel electrophoresis. J Biochem (Tokyo), 1974. 75(2): p. 309-19.
Ibel, et al. Protein-decorated micelle structure of sodium-dodecyl-sulfate-protein complexes as determined by neutron scattering. Eur J Biochem, 1990. 190(2): p. 311-8.
Samso, et al. Evidence for sodium dodecyl sulfate/protein complexes adopting a necklace structure. Eur J Biochem, 1995. 232(3): p. 818-24.
Westerhuis, et al. Reevaluation of the electrophoretic migration behavior of soluble globular proteins in the native and detergent-denatured states in polyacrylamide gels. Anal Biochem, 2000. 284(1): p. 143-52.
Frank, et al. Precision of sodium dodecyl sulfate-polyacrylamide-gel electrophoresis for the molecular weight estimation of a membrane glycoprotein: studies on bovine rhodopsin. Arch Biochem Biophys, 1975. 171(1): p. 1-13.
Maddy, et al. A critical evaluation of the analysis of membrane proteins by polyacrylamide gel electrophoresis in the presence of dodecyl sulphate. J Theor Biol, 1976. 62(2): p. 315-26.
Grefrath, et al. The molecular weight of the major glycoprotein from the human erythrocyte membrane. Proc Natl Acad Sci U S A, 1974. 71(10): p. 3913-6.
Miyake, et al. Isolation of a membrane protein from R rubrum chromatophores and its abnormal behavior in SDS-polyacrylamide gel electrophoresis due to a high binding capacity for SDS. J Biochem, 1978. 83(6): p. 1679-86.
Rath, et al. Detergent binding explains anomalous SDS-PAGE migration of membrane proteins. Proc Natl Acad Sci U S A, 2009. 106(6): p. 1760-1765.
Ulmschneider, et al. Properties of integral membrane protein structures: derivation of an implicit membrane potential. Proteins, 2005. 59(2): p. 252-65.
Rath, et al. Peptides as transmembrane segments: Decrypting the determinants for helix-helix interactions in membrane proteins. Biopolymers, 2007.
Roux, et al. Conformational changes of phospholipid headgroups induced by a cationic integral membrane peptide as seen by deuterium magnetic resonance. Biochemistry, 1989. 28(5): p. 2313-21.
Huschilt, et al. Orientation of alpha-helical peptides in a lipid bilayer. Biochim Biophys Acta, 1989. 979(1): p. 139-41.
Davis, et al. The Interaction between a Synthetic Amphiphilic Polypeptide and Lipids. Biophys J, 1982. 37(1): p. 170-1.
Davis, et al. Interaction of a synthetic amphiphilic polypeptide and lipids in a bilayer structure. Biochemistry, 1983. 22(23): p. 5298-5305.
Lew, et al. The effects of polar and/or ionizable residues in the core and flanking regions of hydrophobic helices on transmembrane conformation and oligomerization. Biochemistry, 2000. 39(32): p. 9632-40.
Lew, et al. The effect of interactions involving ionizable residues flanking membrane-inserted hydrophobic helices upon helix-helix interaction. Biochemistry, 2003. 42(36): p. 10833-42.
Zhuo, et al. Polar residues drive association of polyleucine transmembrane helices. Proc Natl Acad Sci U S A, 2001. 98(5): p. 2250-5.
Zhuo, et al. Interhelical hydrogen bonding drives strong interactions in membrane proteins. Nat Struct Biol, 2000. 7(2): p. 154-60.
Gurezka, et al. A heptad motif of leucine residues found in membrane proteins can drive self-assembly of artificial transmembrane segments. J Biol Chem, 1999. 274(14): p. 9265-70.
Hermanson., Bioconjugate techniques. 2nd Ed. ed. 2008: Academic Press. Chapter 19, pp. 765-773; Chapter 20, 789-793; Chapter 22, pp. 879-883.
Amblard, et al. Fundamentals of modern peptide synthesis. Methods Mol Biol, 2005. 298: p. 3-24.

*Primary Examiner* — Michael Pak

(57) ABSTRACT

The present invention provides a novel membrane protein molecular weight marker.

10 Claims, 5 Drawing Sheets

MOLECULAR WEIGHT MARKERS FOR MEMBRANE PROTEINS

FIELD OF THE INVENTION

The invention relates to molecular weight markers and more particularly to molecular weight markers for membrane proteins.

BACKGROUND OF THE INVENTION

Thousands of labs worldwide are studying helical membrane proteins. These proteins regulate the trafficking of water, ions, and other molecules into and out of the cell.

A host of human diseases are caused by defects in membrane proteins. These proteins are highly hydrophobic molecules that reside in the fatty layer that surrounds all human cells, and control the flow of the materials vital to life in and out of the cell, cellular growth, and regulation. Despite the importance of these molecules in maintaining the health of the human body, research on membrane proteins is in its relative infancy versus their water-soluble protein counterparts. In particular, the study of membrane proteins has been hindered by their insolubility when extracted outside their native membrane environment—a necessary step in the characterization of their function and malfunction. These challenges are evidenced by the extended gaps in the discovery-to-therapeutic pipeline for diseases traceable to membrane protein defects. Cystic fibrosis, for example, is caused by a mutation in the cystic fibrosis transmembrane conductance regulator (CFTR)—a membrane protein—yet remains incurable 20 years after the discovery of the CFTR gene, in large part because technologies appropriate for detailed study of this and other membrane proteins in the laboratory have not been available. Therefore, new research tools specific to the specific physiochemical properties of membrane proteins must be developed.

Since membrane proteins occur largely on the surfaces of cells, they are the major targets accessible to drug action. The relevance of these molecules in drug development is reflected in the large number of therapeutics on the market directed at membrane proteins, which accounted for about 70% of the pharmaceuticals approved by the FDA from 1996-2006. G-protein coupled receptors, for example, have been termed the 'staple diet' of the pharmaceutical industry. It has nevertheless been suggested that certain membrane protein families are relatively under-explored in terms of drug discovery. Membrane protein research thus represents a broad opportunity for the pharmaceutical industry to expand its range of target molecules.

Virtually all human diseases, whether inherited or acquired, are caused when the protein(s) responsible for an important biological activity fail to perform their function. The involvement of membrane proteins in virtually all cellular mechanisms of survival and reproduction make them crucial research targets in the understanding of these mechanisms and the diseases they can engender. Yet, new drugs against such disease-causing molecules in the body cannot be developed until the target molecules have first been identified and characterized.

Membrane proteins represent fully one-third of the human genome. They are key action macromolecules in the human body, serving as enzymes, nutrient transporters, signalling systems, and as participants in a myriad of activities involving vision, smell, taste, cognition, memory, and motion. It is now known that defects or deficiencies in membrane proteins underlie a striking array of human diseases, including, but not limited to, cystic fibrosis, neurological disorders, diabetes, Alzheimer's, multiple sclerosis, muscular dystrophy, heart and kidney diseases, many forms of cancer, and lethal genetic diseases. Membrane proteins are also intermediaries in various modes of bacterial drug resistance in infectious disease, and serve as receptors for infection by viruses such as HIV. Afflictions such as addiction, cognition and memory, depression, and schizophrenia have all been associated with membrane proteins. More than ever, if biological science is to successfully treat human diseases that have thus far evaded our boldest efforts, elucidation of the basic mechanisms that underlie human disease, and how/why these protein molecules become compromised in disease, is an absolute necessity.

Importantly, the challenges inherent in membrane protein production, isolation, identification, and stability are currently yielding to modern molecular biological techniques, and researchers in this field are now poised to make important advances in their understanding of the mechanisms of action of these vital proteins.

Membrane proteins are distinguished from water-soluble proteins by their highly hydrophobic character which necessitates their maintenance in detergents such as sodium dodecylsulfate (SDS) or non-denaturing detergents such as Triton-X100 or dodecylmaltoside for study. The structure of the *S. lividans* KcsA potassium channel exemplifies membrane protein topology. The hydrophobic portions of TM helices are flanked by positively charged residues and/or aromatic residues and are separated by hydrophilic and/or polar loop regions. This amino acid distribution illustrates the general layout of the TM segments of helical membrane proteins.

Proteins of each type can be routinely and productively examined for their purity, size, and stoichiometry on a protein sizing technique known as sodium dodecylsulfate polyacrylamide gel electrophoresis (SDS-PAGE). This procedure, arguably the most commonly used laboratory technique in the world, compares the gel migration distance of the protein(s) of interest to that of commercially available water-soluble protein calibration standards in order to determine molecular weight (MW). While SDS-PAGE typically estimates the sizes of water-soluble proteins with reasonable accuracy, estimates of membrane protein MWs are commonly inaccurate.

These sizing discrepancies can arise from an increased amount of SDS detergent bound to denatured membrane proteins versus the water-soluble polypeptides used for gel calibration, and may also arise as a result of the amount of non-denatured structure in membrane proteins. This work clearly indicates that the commercially available water-soluble protein MW standards universally used to estimate protein size on SDS-PAGE are inappropriate for use with membrane proteins. Accordingly, there is a need to develop a tool to assist in the characterization, purification, and estimation of structural stability of membrane proteins.

SUMMARY OF THE INVENTION

The present invention provides a structural backbone for molecular weight standards for membrane proteins.

The present invention further provides a set of molecular weight markers for membrane proteins that is based on appropriate hydropathy, SDS or other detergent binding, or structure in SDS or other detergents that mimics that of denatured transmembrane proteins.

The present invention further provides a set of molecular weight markers for membrane proteins that are bifunctional protein markers that allow for tailored chemistry of the markers. In one embodiment, the molecular weight markers include Cys residues at both ends of the marker.

The present invention further provides a set of molecular weight markers for membrane proteins that are specific mimics of the properties of transmembrane segments, e.g. molecular weight biomarkers that comprise a transmembrane-integrating hydrophobic peptide core of a length suitable to span a biological membrane bilayer in an alpha-helix orientation.

The present invention further provides a set of molecular weight markers that contain a hydrophobic core sequence comprised of Ala and/or Val and/or Ile and/or Leu residues. In one embodiment the hydrophobic core comprises about 12-25 of these residues. In a further embodiment the hydrophobic core comprises about 17-22 of these residues. In one embodiment the hydrophobic core comprises repeating Leu residues. In one embodiment the hydrophobic core comprises 20 Leu residues. In one embodiment the hydrophobic core comprises 12 Leu residues.

In another embodiment the present invention provides a set of molecular weight markers that comprise a hydrophobic core sequence of Ala and/or Val and/or Ile and/or Leu residues residues, as described above, and further comprise any combination or number of Lys and/or Ser and/or Arg and/or aromatic residues flanking the hydrophobic core sequence. In one embodiment a specific arrangement of Lys and/or Ser residues flanks the hydrophobic core sequence.

In another embodiment the present invention provides a set of molecular weight markers that include the following sequence C-SKSKS-(L)$_n$-SKSKS-C (SEQ ID NO: 1) that provide more than one reactive sulfhydryl site, wherein n=12-25. In one embodiment, the sequence, described above, is repeated with adjacent repeating sequences connected by a linker group.

The present invention further provides a set of peptides comprising the sequence C-SKSKS-(L)$_n$-SKSKS-C, wherein n=12-25. In one embodiment, the peptides provide a set of molecular weight markers for membrane proteins. In another embodiment, the peptides described herein form the core sequence of a series of molecular weight markers for membrane proteins. In another embodiment, the peptides undergo self-polymerization to provide a set of molecular weight markers for membrane proteins.

In another embodiment the present invention provides a membrane protein molecular weight marker comprising the sequence HS-R-S-[BMOE-S-R-SH]$_x$ wherein R comprises Cys-Lys-Ser-Lys-Ser-(Leu)$_n$-Ser-Lys-Ser-Lys-Cys (SEQ ID NO: 2), wherein n=12-25 and x=0-100. In another embodiment the cross linking group BMOE may be any bifunctional cysteine-reactive cross-linking reagent.

The present invention further provides a method for self-polymerization of the core peptide sequences described herein.

The present invention further provides a set of molecular weight markers formed by the self-polymerization method described herein.

The present invention further provides a method for polymerization of a peptide having bifunctional Cys residues, comprising the steps of (i) providing a peptide having Cys residues at the N- and C-terminus; (ii) optionally reducing the peptide by incubation with a sulfhydryl-reducing agent; (iii) cross-linking the Cys residues using a bifunctional sulfhydryl-reactive cross-linking agent; (iv) repeating step (iii) until the desired polymer size is achieved; (v) reducing any unlinked Cys residues; (vi) optionally terminating the reaction with a monofunctional peptide having one Cys residue; and (vii) optionally labelling any unlinked Cys residues.

In one embodiment, the reducing step (ii) is performed using a reducing agent such as TCEP. In another embodiment, the cross-linking step (iii) is performed using a bifunctional maleimide, such as but not limited to: bis(maleimido)ethane (BMOE); 1,4-bismaleimidobutane (BMB); bismaleimidohexane (BMH); 1,8-bis-maleimidodiethyleneglycol (BM(PEG)$_2$); 1,8-bis-maleimidotriethyleneglycol (BM(PEG)$_3$); and 1,6-hexane-bis-vinylsulfone (HBVS).

In an alternative embodiment, the present invention provides a kit comprising at least one molecular weight marker as described herein and instructions for using the kit. The kit may further include at least one reagent and/or buffer.

BRIEF DESCRIPTION OF THE DRAWINGS

The present invention will now be described in further detail with reference to the following figures.

DETAILED DESCRIPTION OF THE PREFERRED EMBODIMENTS

Figure 1:
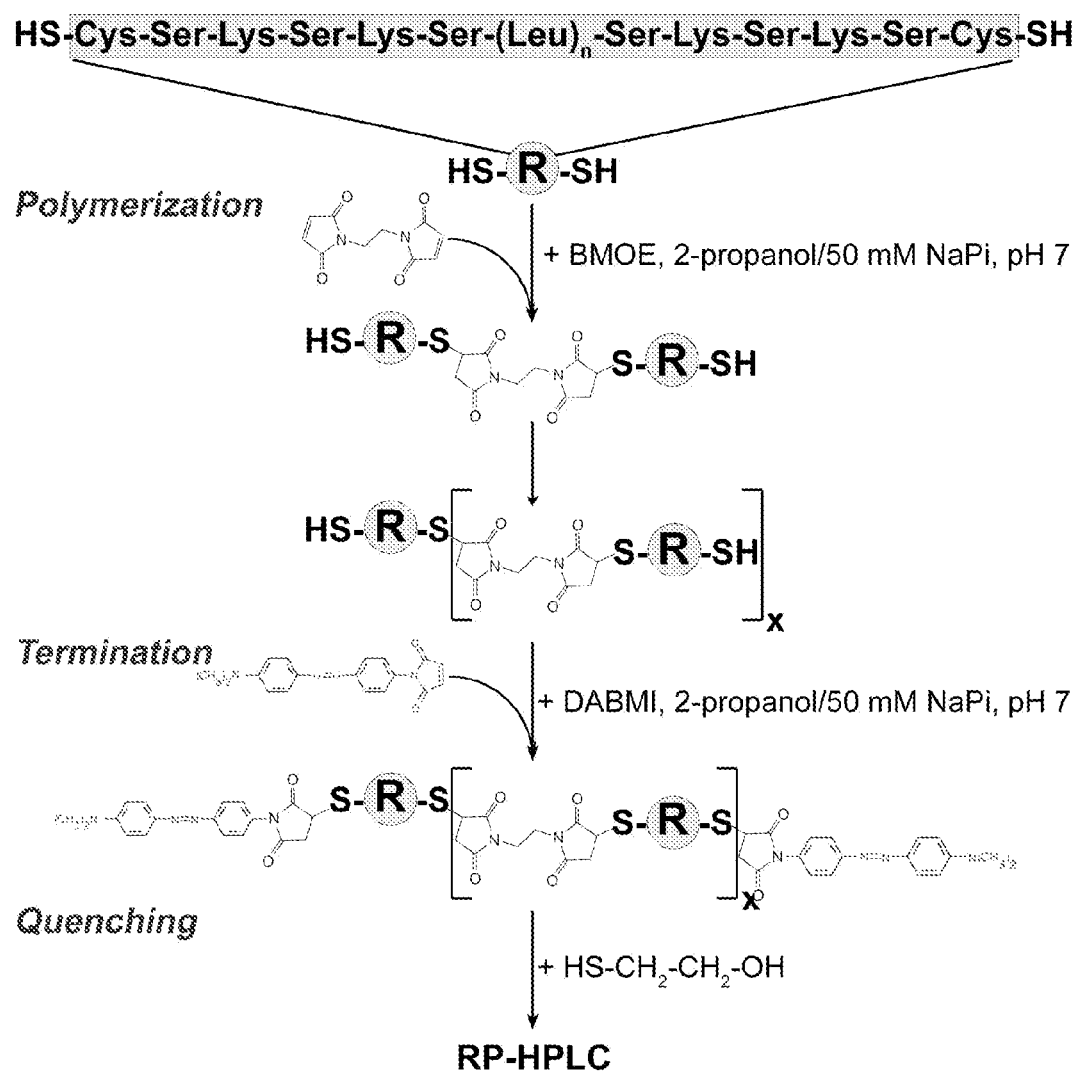
FIG. 1 is a schematic of the production of membrane protein MW standards with a poly-Leu hydrophobic core.

The present invention provides a set of novel molecular weight standards appropriate for SDS-PAGE sizing of denatured membrane proteins, and/or direct indication of non-denatured tertiary and/or quaternary structure. Thus, molecular weight biomarkers that comprise a transmembrane-integrating hydrophobic peptide core of a length suitable to span a biological membrane bilayer in an alpha-helix orientation are provided.

Molecular weight markers in accordance with the invention comprise a core of hydrophobic amino acids, including amino acids with a side chain comprised of a combination of carbon, hydrogen, and/or sulfur atoms such as, alanine, leucine, isoleucine, valine, methionine, and hydrophobic derivatives of any one of these such as, norleucine, phenylglycine, 2-aminobutyric acid, cyclohexylalanine, butylglycine, thienylalanine and cysteine. A preferred marker comprises a poly-Leu core segment to mimic the hydrophobicity, helix-forming propensity, and predominance of Leu in natural transmembrane sequences.

The hydrophobic core of the molecular weight markers may be flanked at either termini with regions similar to those of native transmembrane segments, e.g. comprised of positively charged, and/or aromatic, and/or hydrophilic residues. Thus, the flanking regions may comprise any combination or number of residues such as lysine, arginine, histidine, serine, threonine, asparagine, glutamine, aspartic acid, glutamic acid, and aromatic residues such as tyrosine and tryptophan, at its N- and/or C-termini, and derivatives of any one of these residues such as ornithine, citrulline, homocitrulline, homoserine, β-hydroxyvaline and α-aminosuberic acid.

The present molecular weight markers generally mimic the properties of helical membrane proteins with a hydrophobic core for helix-forming propensity, and termini that mimic the loop regions linking transmembrane regions, inhibiting the aggregation of these peptides, anchoring their ends to the polar surface of bilayers or micelles to assist in membrane-spanning orientations. Thus, the present molecular weight standards are designed to bind SDS at levels comparable to those of denatured membrane proteins.

The molecular weight standards are based on chemically synthesized peptide amides or acids with the base sequence $H_2N$-Cys-Lys-Ser-Lys-Ser-(Leu)$_n$-Ser-Lys-Ser-Lys-Cys-$NH_2$, or $H_2N$-Cys-Lys-Ser-Lys-Ser-(Leu)$_n$-Ser-Lys-Ser-Lys-Cys-COOH, where (Leu)$_n$ is the number of leucine residues. The MW standards therefore have the dual advantage of being based on an amino acid sequence that mimics the universal features of the membrane-spanning segments of membrane proteins, and are likely to have denatured tertiary and/or quaternary contacts in SDS as required for uniform SDS binding levels.

In one embodiment, the peptide sequence, prepared as described above, includes a Leu core where n=12-25. In one embodiment, n=20. The range of 12-25 represents at the low end the minimum number of Leu residues sufficient for transmembrane integration, and at the high end the number of these residues expected to span a biological membrane bilayer in an alpha-helix orientation.

Figure 2A:
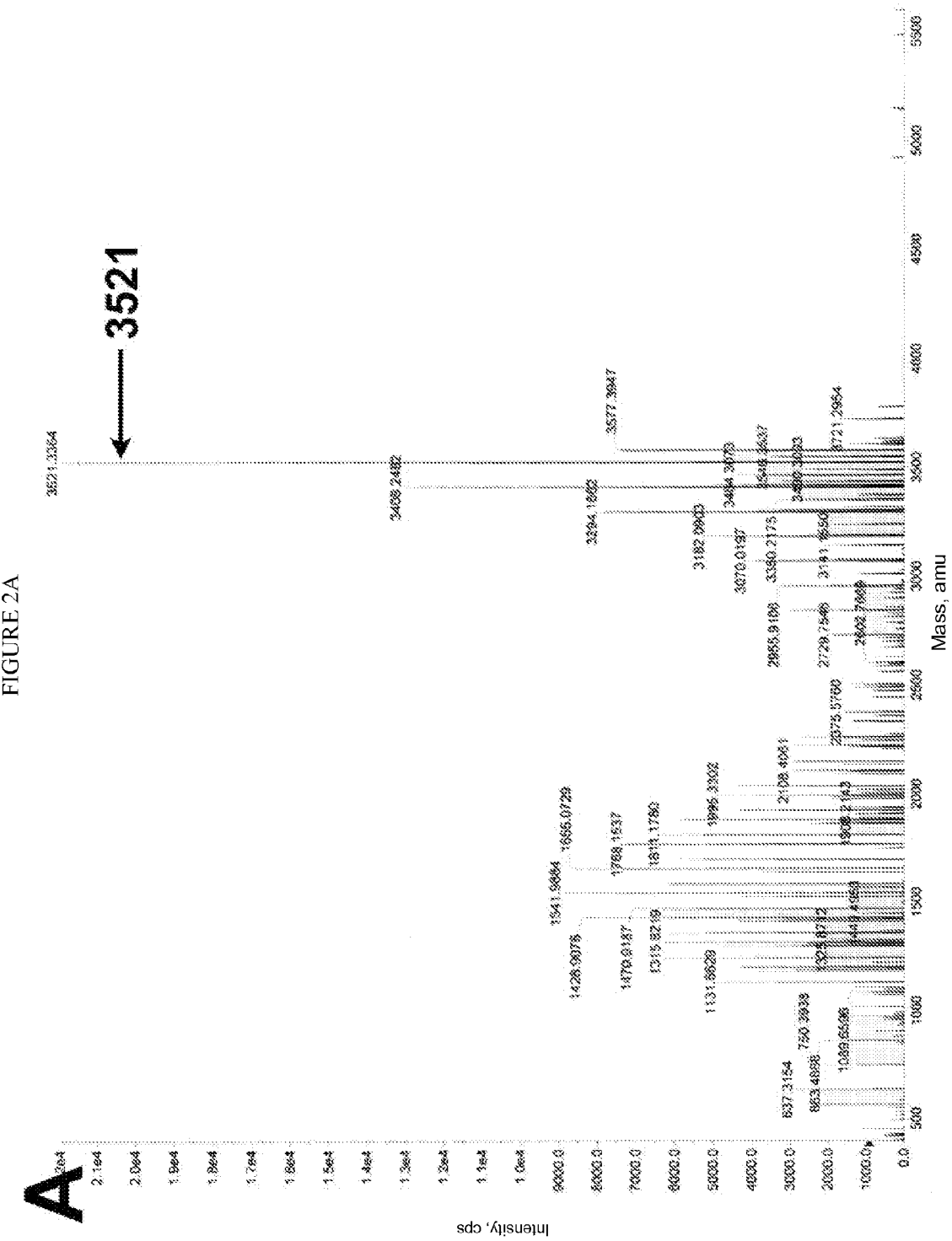
FIG. 2A shows a mass spectrum of peptide embodiments of the present invention where the hydrophobic core residue is Leu and n=20.
Figure 2B:
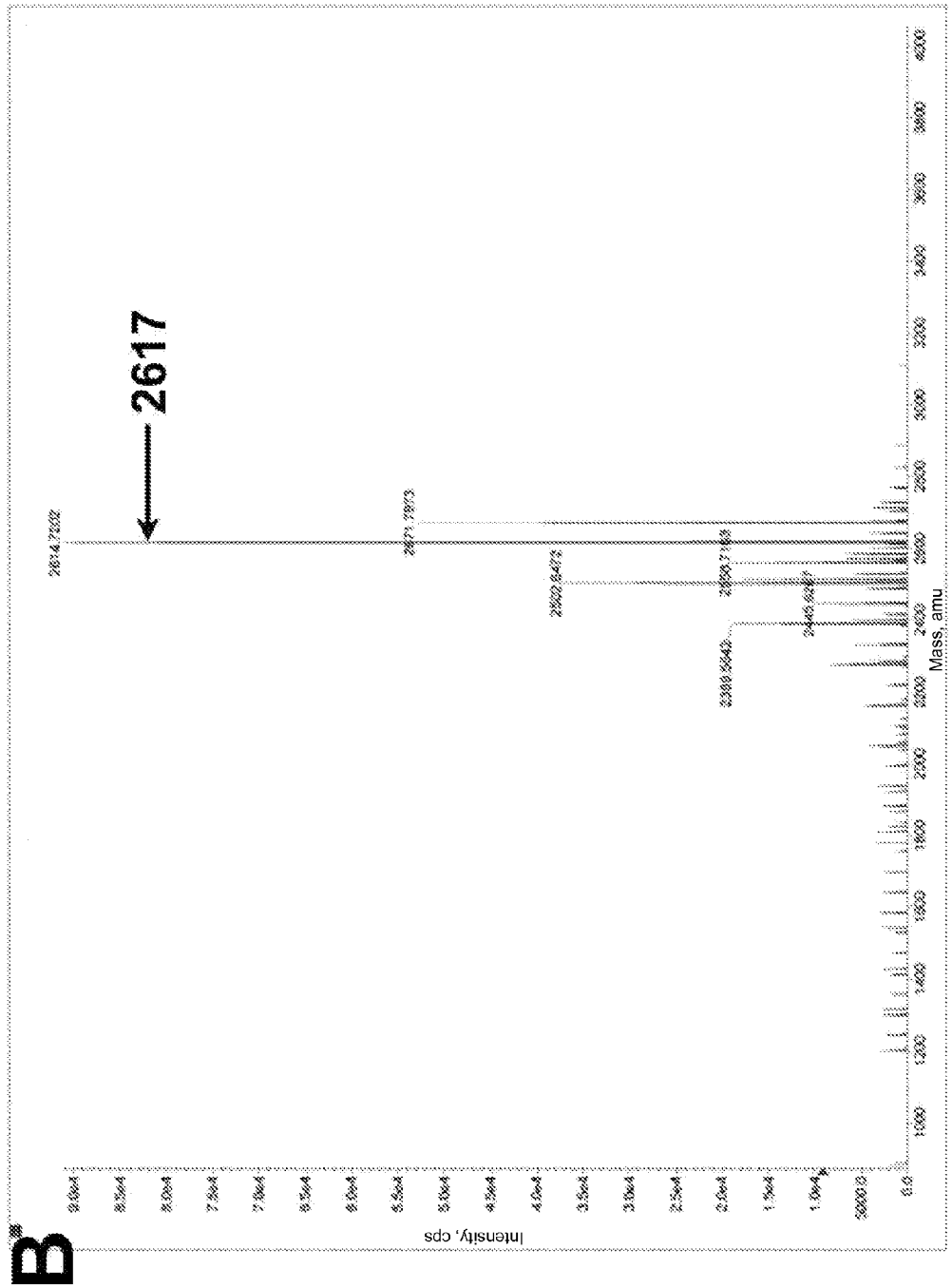
FIG. 2B shows a mass spectrum of peptide embodiments of the present invention where the hydrophobic core residue is Leu and n=12.

The present markers may be synthesized using standard synthetic techniques. For example, Fmoc chemistry may be used, as described by Amblard, M., Fehrentz, J. A., Martinez, J., and Subra, G. (2005) *Methods Mol Biol* 298, 3-24 on a low-load resin that produces an amidated C-terminus upon peptide cleavage with trifluoroacetic acid. Reagents used for peptide synthesis include N,N-dimethylformamide, dichloromethane, piperidine, N,N-diisopropylethylamine, methanol, N-[(dimethylamino)-1H-1,2,3-triazolo[4,5-b]pyridino-1-ylmethylene]-N-methylmethanaminium hexafluorophosphate N-oxide (HATU), and lithium chloride. FIG. 2A illustrates a mass spectrum of an unpurified version of one embodiment of the peptide with n=20. FIG. 2B illustrates a mass spectrum of an unpurified version of one embodiment of the peptide with n=12. Observed peptide molecular weight in daltons are indicated above each peak in each mass spectrum. The position of each desired peptide on the mass spectrum is indicated with an arrow. Peptide formula molecular weights in daltons are indicated to the right of the arrows.

The present molecular weight standards are appropriate for membrane protein size estimates on SDS-PAGE as they include the following properties: (i) amino acid sequences of comparable residue composition, hydrophobicity, and topology to membrane proteins; (ii) a denatured conformation in SDS micelles where all protein-protein tertiary and quaternary contacts are replaced by protein-detergent interactions—and hence the standards themselves do not self-assemble; and (iii) these MW standards bind SDS at levels similar to denatured natural membrane proteins to provide more accurate size estimates than currently available reagents.

The present invention further provides the additional feature of sulfhydryl containing residues, such as Cys residues, at the peptide N-terminus, peptide C-terminus, or at both of the N- and C-termini to permit self-polymerization of the marker peptide to the desired molecular weight range via sulfhydryl-specific chemistries, termination of the polymerization reaction, and/or covalent attachment of dyes or other molecules for standard protein visualization.

A typical self-polymerization reaction scheme according to the present invention is shown in FIG. 1. The sequence of the biomarker peptide has been abbreviated as "R" throughout the reaction scheme, and "x" represents the number of peptide "R" units in a given polymer. Before polymerization and at fixed intervals during polymerization, peptide aliquots are periodically removed from the reaction mixture and terminated by reaction with the DABMI chromophore in order to ensure that peptide monomer and lower-order (e.g. x=1) oligomers are produced. Remaining reactive species in all aliquots are scavenged by β-mercaptoethanol treatment before separation on RP-HPLC. Note that bismaleimide reagents such as BMOE link the peptide monomers together in a linear or trans conformation.

After optional reduction by incubation with a sulfhydryl-reducing agent, such as TCEP [tris(2-carboxyethyl)phosphine] or a similar reducing agent, chemical cross-linking of Cys residues included at the peptide N- and C-terminus is performed with a bifunctional sulfhydryl-reactive cross-linking agent such as bifunctional maleimide [e.g. bis(maleimido)ethane, BMOE]. The geometry of the cross-linker's reactive sites confers a 'necklace-and-bead' or trans conformation to the polymerized species that is believed to expose each poly-Leu peptide to the SDS detergent, as seen in FIG. 1. When the desired polymer size is achieved, any unlinked Cys residues are re-reduced and, optionally reacted with a peptide unit with a single Cys residue at its N- or C-terminus, and if desired, labelled with a sulfhydryl-reactive dye (e.g. the orange dye, 4-dimethylaminophenylazophenyl-4'-maleimide (DABMI)], or labelled with another molecule for detection via a desired visualization method. Peptides are polymerized in various combinations of buffer and organic solvent [e.g. 2-propanol, n-butanol, acetonitrile] to provide the desired molecular weight range, and subsequently labelled in similar media with the desired sulfhydryl-reactive molecule. The SDS-PAGE separation of polymerized peptides according to the present invention was accomplished. The migration positions and MW values (in kDa) of Mark-12 MW standards (Life Technologies) was compared to the migration positions and polymeric size of polymerized peptides, according to the present invention. Results of polymerization reactions in 50%, 30%, and ~20% 2-propanol indicate that the degree of polymerization increased with the % 2-propanol in the reaction mixture. Total polymerization reaction time was ~24 h. The bands were visualized by labelling with DABMI; silver staining was also used to visualize polypeptides.

Following this scheme, several 'low range' MW markers have been prepared encompassing up to ~7 peptide lengths, where the degree of peptide self-polymerization is controlled by the amount of organic solvent present in the reaction mixture. These polymers are soluble in SDS and readily separate into a ladder on SDS-PAGE.

A method of utilizing the present molecular weight standards is also provided. The method comprises dissolution of the present molecular weight standards into an SDS-PAGE sample buffer, application of the desired amount of the dissolved standards to lanes of an SDS-PAGE gel, electrophoresis of the standards through the gel for a set period of time by application of a potential difference, and visualization of the markers. After visualization, the distance migrated from the top of the gel lane by each cross-linked species in the present biomarkers is measured and plotted versus molecular weight to generate a gel calibration curve. The distance migrated on the same gel by analyte proteins is then compared to the calibration curve to estimate molecular weight. In one embodiment, an aliquot of the present biomarkers is removed from the reaction mixture after cross-linking is completed, and solvent evaporated in a stream of $N_2$. The dry biomarkers are dissolved in Life Technologies' NuPAGE® LDS sample buffer with NuPAGE® reducing agent, heated at 70° C. for 10 min, and cooled to room temperature. An aliquot of the prepared biomarkers is then applied to gel electrophoresis in gel boxes and 12% NuPAGE® Bis-Tris gels purchased from Life Technologies. Electrophoresis proceeds at 140 V for 80 min under reducing conditions in NuPAGE® MES SDS running buffer, pH 7.3, with NuPAGE® antioxidant, following the manufacturer's protocols. Analyte proteins are prepared and electrophoresed in the same manner, with the exception that certain analytes are not dried under $N_2$ before dissolution in NuPAGE® LDS sample buffer and are instead diluted from stock solutions in various buffers, and may not be heated before application to the gel. Proteins are visualized using Life Technologies' SilverXpress™ silver staining kit following the manufacturer's protocols. Post-visualization, gels may be scanned to image files. The migration distance from the bottom of the gel lane to the region of highest staining intensity of each biomarker and/or analyte protein may then be measured using image processing software such as ImageJ®, Photoshop®, etc. Molecular weights of biomarker bands are estimated using the formula: MW=[dp*peptide mass]+[(dp−1)*mass of cross-linker], where dp is the degree of polymerization of the biomarker band. The degree of polymerization is determined by counting upwards from the migration distance of the monomeric, uncrosslinked, peptide band. Migration distances are plotted vs. the natural logarithm of MW of each biomarker band to calibrate the gel, and the line of best fit determined. The line of best fit is then used to estimate analyte protein molecular weights from the migration distances of analyte proteins.

Utilization of the standards, described herein, on SDS-PAGE will enable this technique to provide more accurate MW measurements of membrane proteins and to identify residual folding in these molecules.

As stated above, the present invention also provides a kit comprising at least one molecular weight marker as described herein and instructions for using the kit. The kit may further include a pharmaceutically acceptable buffer. The kit may further include, in one container or in separate containers, other reagents useful in the method of the invention as described herein.

While this invention has been described with reference to illustrative embodiments and examples, the description is not intended to be construed in a limiting sense. Thus, various modification(s) of the illustrative embodiments, as well as other embodiments of the invention, will be apparent to persons skilled in the art upon reference to this description. It is therefore contemplated that the appended claims will cover any such modifications or embodiments. Further, all of the claims are hereby incorporated by reference into the description of the preferred embodiments.

Any publications, patents and patent applications referred to herein are incorporated by reference in their entirety to the same extent as if each individual publication, patent or patent application was specifically and individually indicated to be incorporated by reference in its entirety.

Embodiments of the present invention are described in the following specific examples which are not to be construed as limiting.

Example 1

Helical Structure of Monomeric Peptides SDS

Figure 3:
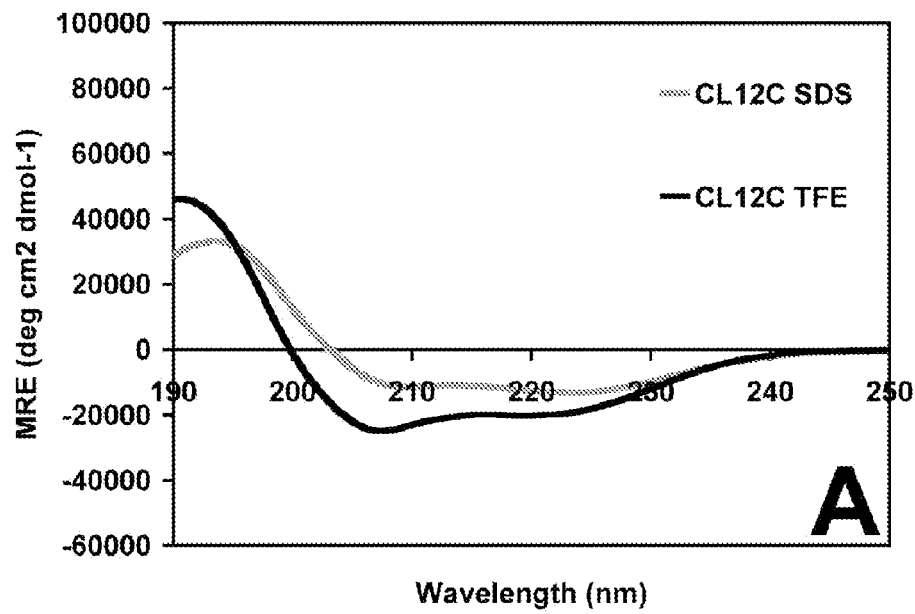
FIG. 3 illustrates CD spectra of monomeric peptides of the present invention where n=12 (CL$_{12}$C) (A) or n=20 (CL$_{20}$C) (B) in SDS (grey curves) and TFE (black curves)
Figure 3:
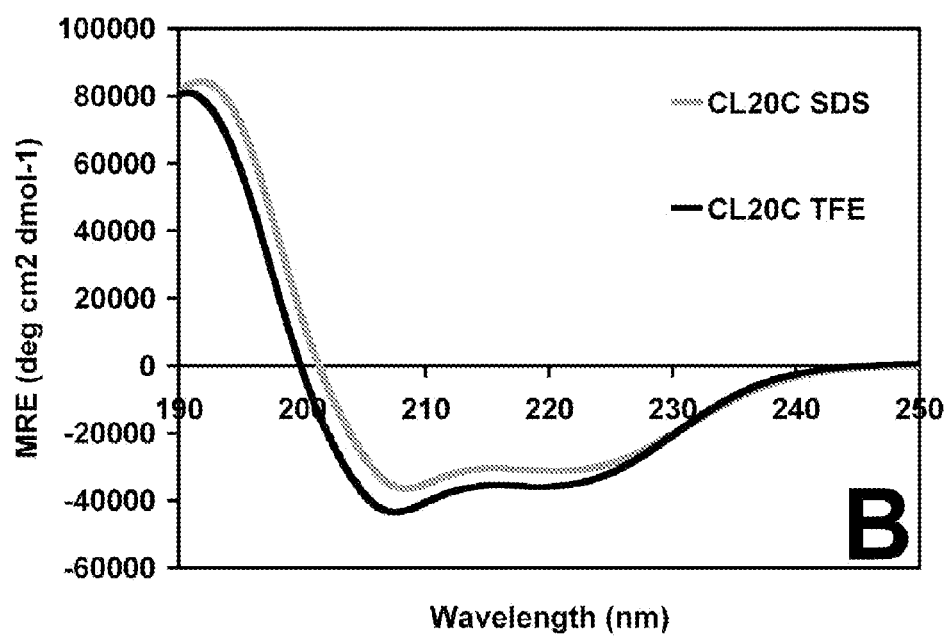

The secondary structure (helix content) of monomeric peptide embodiments of the present invention with n=12 and n=20 was determined using circular dichroism (CD) spectroscopy. Spectra were obtained in 0.3% SDS, 50 mM Na phosphate pH 7, and in pure 2,2,2-trifluoroethanol (TFE), an organic solvent that induces 100% helical conformation in polypeptides. The helicity benchmarks required in SDS are ≥50%, and ≥60%, of the TFE value for n=12 and n=20, respectively, corresponding to the fraction of the peptide sequence encompassed by the poly-Leu sequence designed to mimic the helical transmembrane (TM) regions of membrane proteins. The spectra in SDS of these peptides was found to meet and exceed these benchmark helicity levels as set out in Table 1, below, and illustrated in FIG. 3. CD spectra of the indicated monomeric peptides of the present invention where n=12 ($CL_{12}C$) or n=20 ($CL_{20}C$) in SDS (grey curves) and TFE (black curves). Each spectrum represents the average of 3 independent experiments. All spectra exhibit the dual minima at 208 nm and 222 nm characteristic of helical secondary structure. Relative amounts of helical structure in SDS vs. TFE were evaluated using signal at 222 nm (see Table 1).

TABLE 1

Helicity of monomeric peptides in SDS and TFE

| Peptide | Helicity (at 222 nm, in deg $cm^2$ $dmol^{-1}$) | | In SDS as % TFE |
|---|---|---|---|
| | SDS | TFE | |
| n = 12 | −13,000 | −20,000 | 65 |
| n = 20 | −31,000 | −35,000 | 88 |

Example 2

Procedure for Production of MW Markers Via Bismalemide Cross-Linking

Cross-linking of peptides to degrees of polymerization (dp) of at least 13 was achieved at peptide concentrations of 50-200 µM in an 80% (v/v) TFE aqueous solution buffered at pH 7.5 with 20 mM Tris (the 'reaction buffer'). Cross-linking was performed with a 20-fold molar excess of the Cys-reactive cross-linker bis-maleimidoethane (BMOE) and incubation for 1 hour at room temperature under $N_2$ gas in the dark, followed by supplementation with an additional 20-fold molar excess of BMOE and reaction overnight at 4° C. under $N_2$ in the dark. Here, TFE is utilized as the water-soluble organic solvent for cross-linking. Other water-soluble organic solvents [e.g. 1,1,1,3,3,3-hexafluoro-2-propanol (HFIP), 2-propanol, acetonitrile, methanol] may be substituted as needed.

Stepwise details of the polymerization procedure are as follows:

1. Dissolve poly-Leu peptide in HFIP. Sonicate in bath sonicator 10 min.
2. Aliquot appropriate volume of peptide-HFIP solution to achieve final peptide concentration of 50-200 µM in final reaction mixture into clean tube.
3. Evaporate HFIP at room temperature under stream of $N_2$ gas until dry.
4. Add appropriate volume of TFE to dried peptide in tube to achieve total TFE concentration of 80% (v/v) in final reaction mixture. For example, for a total final reaction volume of 80 µL, dried peptide would be resuspended in 64 µL of TFE.
5. Vortex-mix until peptide is removed from tube sides and resuspended in TFE.

6. Add appropriate volume of water to TFE-peptide solution to top final reaction mixture to volume. For example, for a total final reaction volume of 80 µL, add 8 µL of water. Vortex-mix.
7. Add appropriate volume of 10× buffer (200 mM Tris, pH 7.5) to top final reaction mixture to 1×. For example, for a total final reaction of 80 µL, add 8 µL of 10× buffer. Vortex-mix.
8. Blanket peptide in reaction buffer with $N_2$ and sonicate in bath sonicator for 10 min. Meanwhile, mass 2.2 mg of BMOE to clean tube and dissolve in 250 µL of reaction buffer to form a 40 mM solution.
9. After sonication, add an appropriate volume of 40 mM BMOE (e.g. 8 µL to 80 µL of a 200 µM solution of poly-Leu peptide in reaction buffer). Vortex to mix, blanket reaction with $N_2$, and nutate in the dark at room temperature for 1 h.
10. At 1 h, repeat addition of BMOE as above, except incubate at 4° C. overnight. At this time, reducing agent(s) [e.g. 2-mercaptoethanol, dithiothreitol, tris(2-carboxyethyl) phosphine, etc.] at a final concentration of 10-50 mM may be added to the solution of cross-linked peptides. Approximately 0.3 µL of the 200 µM solution is sufficient to produce intense bands on a silver-stained gel.

Figure 4:
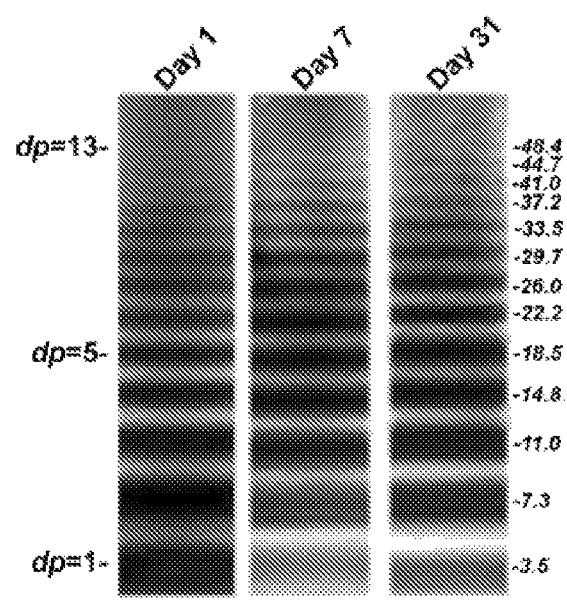
FIG. 4 illustrates the SDS-PAGE separation and shelf life of polymerized n=20 peptide.

SDS-PAGE separations on Life Technologies 12% NuPAGE MES-Tris gels of the n=20 polymerized peptide is shown in FIG. 4 with the degree of polymerization (dp) indicated at left and MW (kDa) at right. Bands were visualized using Life Technologies' SilverXpress silver staining kit. There was no significant change in the gel pattern after 31 days.

This cross-linked preparation was used to calibrate SDS-PAGE without purification, and maintained a consistent level of SDS-PAGE separation and silver staining after storage without further purification at 4° C. under $N_2$ for at least 4 weeks.

Example 3

Efficacy in SDS-Page Estimation of Membrane Protein MWs

The present biomarkers have been tested for the ability to estimate the molecular weight of membrane proteins on SDS-PAGE where n=12 or n=20 peptides were polymerized. SDS-PAGE estimates of membrane protein molecular weights were compared to estimates achieved with a state-of-the-art reagent comprised of water-soluble proteins (Life Technologies' Mark-12™ Unstained Standards). SDS-PAGE was performed on Life Technologies' 12% NuPAGE™ precast gel system in MES-Tris buffer under reducing conditions following the manufacturer's protocols. Analyte proteins and polymerized MW biomarkers of the present invention where n=12 or n=20 were prepared in NuPAGE™ LDS sample buffer under reducing conditions according to the manufacturer's protocols. The Life Technologies' SilverXpress™ staining kit was used to image analyte and standard proteins after SDS-PAGE. Gels were calibrated with the biomarkers by plotting the natural logarithm of biomarker vs. distance in mm from the well bottom to the centre of staining intensity of each band, and determining the line of best fit. SDS-PAGE separation of the polymerized MW biomarkers of the present invention where n=12 or n=20 was compared to separation of Mark-12™ standards. The migration positions of these markers are significantly different, such that they calibrate SDS-PAGE differently. This is the key property of the present invention that corrects SDS-PAGE calibration for membrane proteins.

The first set of proteins tested were selected proteins from a library of wild-type (WT) and mutant forms of a model membrane protein derived from transmembrane (TM) segments 3 and 4 of the cystic fibrosis transmembrane conductance regulator (termed CFTR TM3/4 or 'TM3/4') that was previously shown to deviate in MW by up to ~30% from actual values on SDS-PAGE calibrated with Mark-12™ as described in Rath et al. *Proc Natl Acad Sci USA* 2009, 106, 1760-1765. SDS-PAGE was performed in the gels and buffers as described, but gels were run for 80 min instead of 100 min to ensure that the dp=0 embodiments of the present MW biomarkers were retained on the gels, and silver staining was used to visualize proteins. Calibration with the present MW biomarkers where n=20 significantly increased by ~2-fold the accuracy of MW determination vs. the state-of-the-art Mark-12™ product among a group of TM3/4 proteins (Table 2).

TABLE 2

MW estimation on SDS-PAGE of selected CFTR-based model membrane proteins

| CFTR TM3/ | | Deviation from actual MW (%)[a] | | |
|---|---|---|---|---|
| 4 Protein | MW (kDa) | Mark-12 | n = 12 Leu | n = 20 Leu |
| WT | 9.44 | 13 | 16 | 6.5 |
| E217F | 9.45 | 6.6 | 7.2 | 2.3 |
| E217V | 9.41 | 7.6 | 8.3 | 1.0 |
| G228L | 9.49 | 9.8 | 11 | 1.7 |
| V232A | 9.41 | 15 | 17 | 8.9 |
| V232K | 9.47 | 13 | 15 | 6.3 |
| Average[b]: | | 11 | 12 | 4.5 |

[a]Calculated as the absolute value of (Estimated MW − Actual MW)/(Actual MW) × 100% of at least 3 independent experiments on SDS-PAGE calibrated with the indicated standards.
[b]By ANOVA, deviations in SDS-PAGE estimates of MW are reduced by calibration with n = 20 Leu MW markers vs. Mark-12 ™ (p = 8.59 × 10$^{-8}$); n = 12 Leu MW markers and Mark-12 ™ were identical (p = 0.303).

Application of natural membrane proteins to SDS-PAGE calibrated with Mark-12™, or with MW standards of the present invention where n=12 or n=20 showed that the n=20 embodiment reduced deviations in estimated MW by 3-fold compared to Mark-12 ™ (Table 3). SDS-PAGE calibration with the present invention in the embodiment where the polymerized peptide has n=20 Leu residues therefore provides a significant reduction in sizing errors when the technique is applied to membrane proteins compared to a state-of-the-art product.

TABLE 3

MW estimation on SDS-PAGE of selected natural membrane proteins

| | | Deviation from actual MW (%)[c] | | |
|---|---|---|---|---|
| Protein[a,b] | MW (kDa) | Mark-12 | n = 12 Leu | n = 20 Leu |
| EmrE Monomer | 15 | 18 | 16 | 9.2 |
| EmrE Dimer | 30 | 17 | 15 | 8.5 |
| Hsmr Dimer | 29 | 19 | 14 | 3.1 |
| PLB Pentamer | 13 | 2.5 | 4.1 | 8.0 |
| DM-20 | 26 | 25 | 22 | 8.5 |

TABLE 3-continued

MW estimation on SDS-PAGE of selected natural membrane proteins

| Protein[a,b] | MW (kDa) | Deviation from actual MW (%)[c] | | |
|---|---|---|---|---|
| | | Mark-12 | n = 12 Leu | n = 20 Leu |
| PLP | 30 | 20 | 16 | 4.1 |
| Average: | | 19 | 16 | 5.8 |

[a] Abbreviations: EmrE, *E. coli* small multidrug resistance protein; Hsmr, *H. salinarum* small multidrug resistance protein; PLB, residues 31-52 of cardiac regulatory protein phospholamban; DM-20, myelin proteolipid protein isoform DM-20; PLP, myelin proteolipid protein.
[b] References identifying the oligomeric sizes of these proteins are as follows: EmrE (Chen, Y. J. et al. *Proc Natl Acad Sci USA* 2007, 104, 18999-19004); Hsmr (Ninio, S. and Schuldiner, S. *J Biol Chem* 2003, 278, 12000-12005); PLB (Oxenoid, K. and Chou, J. J. *Proc Natl Acad Sci USA* 2005, 102, 10870-10875; Karim, C. B. et al. *J Biol Chem* 2001, 276, 38814-38819).
[c] Calculated as the absolute value of (Estimated MW − Actual MW)/(Actual MW) × 100% of 3-6 independent experiments on SDS-PAGE calibrated with the indicated standards.
[d] By ANOVA, deviations in SDS-PAGE estimates of MW are reduced by calibration with n = 20 Leu markers vs. Mark-12 ™ (p = 8.64 × 10$^{-11}$); n = 12 Leu markers and Mark-12 ™ were identical (p = 0.145).

We claim:

1. A membrane protein molecular weight marker comprising a transmembrane integrating hydrophobic peptide core of a length suitable to span a biological membrane bilayer in an alpha-helix orientation wherein the hydrophobic core comprises Leu flanked by any combination or number of residues selected from a group consisting of Lys, Ser, Arg and aromatic residues at hydrophobic core N- and/or C-termini, wherein the molecular weight marker comprises Cys residues at the molecular weight marker's N- and C-terminus.

2. The molecular weight marker according to claim 1 comprising a single Cys residue at the N- or C- terminus.

3. A molecular weight marker as defined in claim 1 wherein the hydrophobic core comprises 12-25 residues.

4. The molecular weight marker according to claim 3 wherein the hydrophobic core comprises 17-22 residues.

5. The molecular weight marker according to claim 3 wherein the hydrophobic core comprises 20 Leu residues.

SEQUENCE LISTING

```
<160> NUMBER OF SEQ ID NOS: 2

<210> SEQ ID NO 1
<211> LENGTH: 37
<212> TYPE: PRT
<213> ORGANISM: Artificial Sequence
<220> FEATURE:
<223> OTHER INFORMATION: molecular weight marker
<220> FEATURE:
<221> NAME/KEY: MISC_FEATURE
<222> LOCATION: (7)..(32)
<223> OTHER INFORMATION: Leu may be repeated 12-25 times

<400> SEQUENCE: 1

Cys Ser Lys Ser Lys Ser Leu Leu Leu Leu Leu Leu Leu Leu Leu Leu
1               5                   10                  15

Leu Leu Leu Leu Leu Leu Leu Leu Leu Leu Leu Leu Leu Leu Leu Ser
                20                  25                  30

Lys Ser Lys Ser Cys
            35

<210> SEQ ID NO 2
<211> LENGTH: 35
<212> TYPE: PRT
<213> ORGANISM: Artificial Sequence
<220> FEATURE:
<223> OTHER INFORMATION: molecular weight marker
<220> FEATURE:
<221> NAME/KEY: MISC_FEATURE
<222> LOCATION: (6)..(30)
<223> OTHER INFORMATION: Leucine may be repeated 12-25 times

<400> SEQUENCE: 2

Cys Lys Ser Lys Ser Leu Leu Leu Leu Leu Leu Leu Leu Leu Leu
1               5                   10                  15

Leu Leu Leu Leu Leu Leu Leu Leu Leu Leu Leu Leu Leu Leu Ser Lys
                20                  25                  30

Ser Lys Cys
        35
```

6. The molecular weight marker according to claim 2 wherein the hydrophobic core comprises 12 Leu residues.

7. The molecular weight marker of claim 1 comprising the sequence Cys-Lys-Ser-Lys-Ser-(Leu)$_n$-Ser-Lys-Ser-Lys-Cys (SEQ ID NO: 2), wherein n=12-25.

8. A membrane protein molecular weight marker as defined in claim 1 comprising the sequence HS-R-S-[CLR-S-R-SH]$_x$ wherein R comprises Cys-Lys-Ser-Lys-Ser-(Leu)$_n$-Ser-Lys-Ser-Lys-Cys (SEQ ID NO: 2), wherein n=12-25, and x=0-100, and CLR can be any bifunctional cysteine-reactive cross-linking reagent.

9. A kit comprising at least one molecular weight marker according to claim 1 and instructions for using the kit.

10. The kit according to claim 9 further comprising at least one reagent and/or buffer.

* * * * *